United States Patent [19]

Brown et al.

[11] Patent Number: 5,082,841
[45] Date of Patent: Jan. 21, 1992

[54] 3-CARBONYL-4-AMINO-8-SUBSTITUTED QUINOLINE COMPOUNDS USEFUL IN INHIBITING GASTRIC ACID SECRETIONS.

[75] Inventors: Thomas H. Brown; Robert J. Ife; Colin A. Leach, all of Welwyn, England

[73] Assignee: SmithKline Beecham Intercredit B.V., Welwyn Garden City, England

[21] Appl. No.: 564,218

[22] Filed: Aug. 7, 1990

[30] Foreign Application Priority Data

Aug. 10, 1989 [GB] United Kingdom ............... 8918265

[51] Int. Cl.$^5$ .................... C07D 215/42; A61K 31/47
[52] U.S. Cl. ........................ 514/235.2; 514/255; 514/313; 544/128; 544/363; 546/159; 546/160; 546/161; 546/162
[58] Field of Search ............ 546/159, 160, 161, 162; 544/128, 363; 514/233.5, 313, 255, 235.2

[56] References Cited

U.S. PATENT DOCUMENTS

| | | | |
|---|---|---|---|
| 3,470,186 | 9/1969 | Hanifin et al. | 546/157 |
| 4,343,804 | 8/1982 | Munson, Jr. et al. | 546/159 |
| 4,789,678 | 12/1988 | Effland et al. | 546/159 |
| 4,806,549 | 2/1989 | Ife et al. | 514/313 |
| 4,806,550 | 2/1989 | Ife et al. | 514/313 |
| 4,808,598 | 2/1989 | Canfield et al. | 546/159 |
| 4,935,431 | 6/1990 | Ife et al. | 514/301 |
| 5,006,535 | 1/1991 | Ife et al. | 514/313 |

FOREIGN PATENT DOCUMENTS

| | | |
|---|---|---|
| 0245054 | 11/1987 | European Pat. Off. |
| 0258755 | 9/1988 | European Pat. Off. |
| 330485 | 8/1989 | European Pat. Off. |
| 339768 | 11/1989 | European Pat. Off. |
| 342775 | 11/1989 | European Pat. Off. |

OTHER PUBLICATIONS

Hanifin et al., J. Med. Chem., 1969, 12, 1096.

*Primary Examiner*—Bernard Dentz
*Assistant Examiner*—Zinna Northington-Davis
*Attorney, Agent, or Firm*—Linda E. Hall; Stuart R. Suter; Edward T. Lentz

[57] ABSTRACT

Aminoquinoline derivatives are described as inhibitors of the $H^+K^+$ATPase enzyme useful in the treatment of gastric acidity. A compound of the invention is 3-butyryl-4-(2-methylphenylamino)-8-(3-dimethylaminopropoxy)quinoline.

18 Claims, No Drawings

3-CARBONYL-4-AMINO-8-SUBSTITUTED QUINOLINE COMPOUNDS USEFUL IN INHIBITING GASTRIC ACID SECRETIONS.

The present invention relates to novel substituted quinoline derivatives, processes for their preparation, intermediates useful in their preparation, pharmaceutical compositions containing them and their use in therapy.

Accordingly, the present invention provides, in a first aspect, a compound of structure (I):

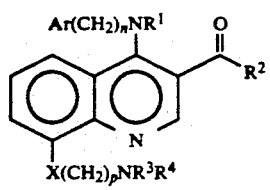

in which
Ar is a phenyl group optionally substituted by 1 to 3 substituents selected from $C_{1-6}$alkyl, $C_{1-6}$alkoxy, amino, $C_{1-6}$-alkylthio, halogen, cyano, hydroxy, carbamoyl, carboxy, $C_{1-6}$alkanoyl or trifluoromethyl;
n is 0 to 4;
$R^1$ is hydrogen or $C_{1-6}$alkyl;
$R^2$ is hydrogen, $C_{1-6}$alkyl, $C_{1-6}$alkoxy, $C_{1-6}$alkoxyC$_{1-6}$-alkyl, $C_{3-6}$cycloalkyl, $C_{3-6}$cycloalkylC$_{1-6}$alkyl, phenyl, phenylC$_{1-6}$alkyl, the phenyl groups being optionally substituted;
X is a bond, CHOH, $NR^1$, S, or O;
p is 1 to 6; and
$R^3$ and $R^4$ are the same or different and are each hydrogen, $C_{1-4}$alkyl, or optionally substituted phenylC$_{1-4}$alkyl or together with the nitrogen atom to which they are attached form a ring, optionally containing one or more further heteroatoms,
or a salt thereof.

Suitably Ar is phenyl or a phenyl group substituted by 1 to 3 substituents selected from $C_{1-6}$alkyl, $C_{1-6}$alkoxy, amino, $C_{1-6}$alkylthio, halogen, cyano, hydroxy, carbamoyl, carboxy, $C_{1-6}$alkanoyl, trifluoromethyl. Preferably Ar is a phenyl group substituted by a single substituent in the 2-position of the phenyl ring or two substitutents in the 2- and 4-positions of the phenyl ring. More preferably, Ar is a phenyl group substituted by a $C_{1-6}$alkyl or $C_{1-6}$alkoxy group for example a methyl or methoxy group in the 2-position of the ring or a $C_{1-6}$alkyl or $C_{1-6}$alkoxy group in the 2-position in combination with a halogen substituent in particular fluoro in the 4-position of the ring. Most preferably, Ar is a phenyl group substituted by a $C_{1-6}$alkyl or $C_{1-6}$alkoxy group in the 2-position of the ring.

Suitably n is 0 to 4; preferably n is 0 or 1; most preferably n is 0.

Suitably, $R^1$ is hydrogen or $C_{1-4}$alkyl, preferably hydrogen.

Suitably, $R^2$ is hydrogen, $C_{1-4}$alkyl, $C_{1-6}$alkoxy, $C_{1-6}$alkoxyC$_{1-6}$alkyl, $C_{3-6}$cycloalkyl, $C_{3-6}$cycloalkylC$_{1-6}$alkyl, phenyl or phenylC$_{1-6}$alkyl, the phenyl groups being optionally substituted. Preferably $R^2$ is $C_{1-6}$alkyl, $C_{1-6}$alkoxy, $C_{3-6}$cycloalkyl or $C_{3-6}$cycloalkyl-C$_{1-6}$alkyl. Most preferably $R^2$ is $C_{1-6}$alkyl, in particular ethyl, isopropyl or n-propyl.

Suitably X is a bond, $NR^1$, S, O or CHOH; preferably X is O.

Suitably p is 1 to 6; preferably p is 1 to 3, most preferably 2 or 3.

Suitably $R^3$ and $R^4$ are the same or different and are each hydrogen, $C_{1-4}$alkyl or optionally substituted phenylC$_{1-4}$alkyl, or together form a ring such as a pyrrolidino, piperidino, piperazino or morpholino ring. Preferably $R^3$ and $R^4$ are the same and are both $C_{1-4}$alkyl or one is $C_{1-4}$alkyl and the other is optionally substituted phenylC$_{1-4}$alkyl, most preferably unsubstituted phenylC$_{1-4}$alkyl.

$C_{1-6}$alkyl groups (either alone or as part of another group) and the alkylene chain $(CH_2)_p$ can be straight or branched.

PhenylC$_{1-6}$alkyl groups e.g. $Ar(CH_2)_n$- include for example the benzyl, phenylethyl, phenylpropyl and phenylbutyl groups; and groups in which the alkyl portion is branched e.g. 1-methylbenzyl.

It will be appreciated that compounds of structure (I) in which one or more of $R^1$ to $R^4$ is a $C_{3-6}$alkyl group (either alone or as part of another group) may contain an asymmetric centre due to the presence of the $C_{3-6}$alkyl group. Similarly, compounds of structure (I) in which X is CHOH will also contain an asymmetric centre. Such compounds will exist as optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form salts, in particular pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

In a further aspect, the present invention provides a process for the preparation of a compound of structure (I) which comprises (a) for compounds of structure (I) in which X is O, S or $NR^1$ reaction of a compound of structure (II) with an amine of structure (III)

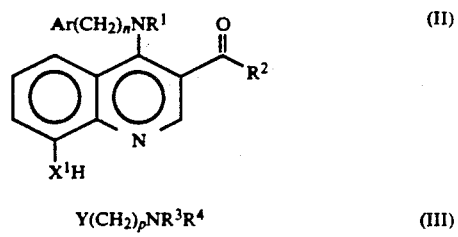

in which Ar, n, $R^1$, $R^2$, p, $R^3$ and $R^4$ are as described for structure (I), $X^1$ is O, S or $NR^1$ and Y is a leaving group;

(b) for compounds of structure (I) in which X is CHOH and n is !, reaction of a compound of structure (IV)

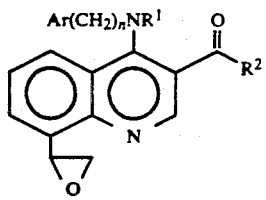

in which Ar, n, $R^1$ and $R^2$ are as described for structure (I), with an amine of structure $HNR^3R^4$ in which $R^3$ and $R^4$ are as described for structure (I);

(c) for compounds of structure (I) in which X is NH, reaction of a compound of structure (V)

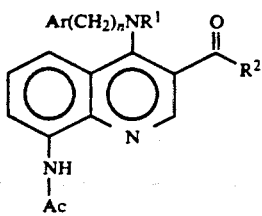

in which Ar, n and $R^2$, are as described for structure (I) and Ac is an acyl group, for example, an acetyl or trifluoroacetyl group, with a compound of structure (III) in the presence of a base;

(d) reaction of a compound of structure (VI)

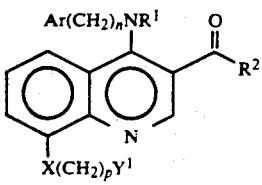

in which Ar, n, $R^1$, $R^2$, X and p are as described for structure (I) and $Y^1$ is a leaving group, with an amine of structure $HNR^3R^4$; or (e) reaction of a compound of structure (VII)

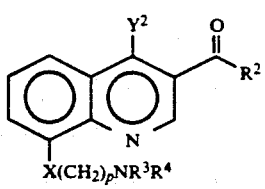

in which $R^2$, X, p, $R^3$ and $R^4$ are as described for structure (I) and $Y^2$ is a leaving group, with a compound of structure $Ar(CH_2)_nNR^1H$ (VIII), in which Ar, n and $R^1$ are as described for structure (I);

(f) for compounds of structure (I) in which X is NH reaction of a compound of structure (IX)

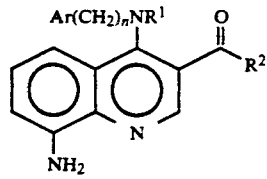

in which Ar, n, $R^1$ and $R^2$, are as described for structure (I); with an aldehyde of structure $OCH(CH_2)_{p-1}NR^3R^4$ (X) in which p, $R^3$ and $R^4$ are as described for structure (I) under reductive alkylation conditions, and optionally thereafter forming a salt.

Suitable leaving groups Y, $Y^1$ and $Y^2$ will be apparent to those skilled in the art and include for example halo, preferably chloro or bromo, mesylate and tosylate. Preferably Y, $Y^1$ and $Y^2$ are halo, in particular chloro.

The reaction between compounds of structure (II) in which $X^1$ is O or S, and compounds of structure (III) is carried out in the presence of a base in an organic solvent at a temperature of between ambient and reflux temperature of the solvent used. Suitable solvents include, for example, tetrahydrofuran, dioxan or dimethylformamide, preferably dimethylformamide. Suitable bases include, for example, potassium carbonate and potassium t-butoxide Preferably potassium t-butoxide. Preferably the reaction is carried out in dimethylformamide in the presence of potassium t-butoxide at a temperature of between about 70° and about 120° C. The reaction between compounds of structure (II) in which $X^1$ is $NR^1$, and compounds of structure (III) is preferably carried out under fusion conditions, i.e. in the absence of a base and solvent.

The reaction between compounds of structure (IV) and an amine $NHR^3R^4$ is carried out in an inert organic solvent at a temperature of between ambient and reflux temperature of the solvent used. Suitable solvents include for example, dimethyl sulphoxide or industrial methylated spirits.

The reaction between compounds of structure (V) and compunds of structure (III) can be carried out in the presence of a base in an organic solvent at a temperature of between ambient and reflux temperature of the solvent used. Suitable solvents include for example, tetrahydrofuran, dioxan or dimethylformamide. Suitable bases include, for example sodium hydride.

The reaction between compounds of structure (VI) and amines of structure $HNR^3R^4$ can be carried out under the same or similar conditions to those described for reaction between compounds of structure (IV) and the same amines.

The reaction between compounds of structure (VII) and an amine of structure $Ar(CH_2)_nNHR^1$ (VIII) is suitably carried out in the presence or absence of an inert solvent at elevated temperature. Suitable solvents include, for example, $C_{1-4}$alkanols such as isopropanol or butanol, and dioxan.

The reaction between compounds of structure (IX) and compounds of structure (X) under reductive alkylation conditions can be carried out, for example, in a solvent such as a $C_{1-4}$alkanol in the presence of a suitable reducing agent such as sodium cyanoborohydride or alternatively using catalytic hydrogenation in the presence of a noble metal catalyst such as platinum or palladium on charcoal.

The intermediates of structures (IV), (V), (VI), (VII) and (IX) can be prepared by standard techniques. For example, the intermediates of structure (II) can be prepared using the procedures outlined in co-pending European Patent Application No. 89301804.4; the intermediates of structure (IV) can be prepared by the methods described hereinafter in the specific examples; the intermediates of structure (V) can be prepared from the corresponding 8-amino precursors, by reaction with, for example, trifluoroacetic anhydride or acetic acid; and intermediates of structure (VI) can be prepared from the corresponding compounds of structure (III) by reaction with a suitable compound of structure $Y(CH_2)_pY^1$ in which Y and $Y^1$ are both leaving groups.

The intermediates of structure (III), (VIII) and (X) are commercially available or can be prepared by standard techniques.

The compounds of structure (I) and their pharmaceutically acceptable salts exert an anti-secretory effect by inhibition of the gastrointestinal H+K+ATPase enzyme (Fellenius, E., Berglindh, T., Sachs, G., Olke, L., Elander, B., Sjostrand, S.E., and Wallmark, B., 1981, Nature, 290, 159-61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In addition to the anti-ulcer properties the compounds of structure (I) are expected to be of use in medicine as inhibitors of bone resorption. In normal subjects there is a balance between bone resorption and bone formation, however, in subjects with bone affected diseases such as osteoporosis, Paget's disease and hyperparathyroidism and related disorders this balance is disturbed. As a consequence of this imbalance the subject suffers a loss of bone tissue, decreased bone mass and bone fragility which can result in fracturing of bones. Bone resorption (or bone loss) is associated with the activity of osteoclast cells, and it is thought that agents which inhibit the activity of such cells (and so inhibit bone resportion) will have a beneficial effect on the reduction of bone loss and be of benefit in the treatment of the above-noted disease states. The present compounds are thus expected to be inhibitors of osteoclast activity and bone resorption and also to be of use in medicine in the treatment of diseases in which bone loss is a factor, in particular osteoporosis, Paget's disease and hyperporathyroidism.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

When used for the treatment of gastro-intestinal diseases and other conditions caused or exacerbated by gastric acidity the pharmaceutically acceptable compounds of the invention will normally be administered in a daily dosage regimen for an adult patient of, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day.

Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

EXAMPLE 1

Preparation of 3-butyrvy-4-(2-methylphenylamino)-8-(3-dimethylaminopropoxy)quinoline 3-Butyryl-4-(2-methylphenylamino)-8-hydroxyquinoline (3.20 g, 10 mmol) and potassium t-butoxide (3.05 g, 25 mmol) were dissolved in dimethyl formamide (30 ml), warmed to 80° and 3-dimethylaminopropyl chloride hydrochloride (1.90 g, 12 mmol) added. The mixture was stirred for 1 hour at 80° then a further portion of potassium t-butoxide (2.44 g, 20 mmol) and 3-dimethylaminopropyl chloride hydrochloride (1.58 g, 10 mmol) added. After a further 2 hours at 80° the mixture was poured into water, extracted with ether and the ether extracts dried and evaporated. Chromatography (silica gel, 5% methanolic ammmonia in dichloromethane) and recrystallisation from ethyl acetate gave 3-butyryl-4-(2-methylphenylamino)-8-(3-dimethylaminopropoxy)quinoline (1.80 g, 88%), m.p. 109°-110°.

|  | $C_{25}H_{31}N_3O_2$ |
|---|---|
| Found | C 74.02, H 7.59, N 10.21 |
| Requires | C 74.04, H 7.70, N 10.36 |

EXAMPLE 2

Preparation of 3-butyryl-4-(4-fluoro-2-methylphenylamino)-8-(3-dimethylaminopropoxy)quinoline 3-Butyryl-4-(4-fluoro-2-methylphenylamino)-8-hydroxyquinoline (3.38 g, 10 mmol) and potassium t-butoxide (3.05 g, 25 mmol) were dissolved in dimethyl formamide (30 ml), warmed to 70° and 3-dimethylaminopropyl chloride hydrochloride (1.90 g, 12 mmol) added. The mixture was stirred for 1 hour at 80° then a further portion of potassium t-butoxide (2.44 g, 20 mmol) and 3-dimethylaminopropyl chloride hydrochloride (1.58 g, 10 mmol) added, and stirring continued overnight. A third portion of potassium t-butoxide (2.44 g, 20 mmol) and 3-dimethylaminopropyl chloride hydrochloride (1.58 g, 10 mmol) was added and the temperature raised to 85°. After a further 5 hours the mixture was poured into water, extracted with ether and the ether extracts dried and evaporated. Chromatography (silica gel, 4-6% methanolic ammmonia in dichloromethane) and recrystallisation from ethyl acetate gave 3-butyryl-4-(4-fluoro-2-methylphenyl-amino)-8-(3-dimethylaminopropoxy)quinoline (0.46 g, 11%), m.p. 99°-100°.

|  | $C_{25}H_{30}FN_3O_2$ |
|---|---|
| Found | C 70.71, H 7.31, N 9.75 |
| Requires | C 70.90, H 7.14, N 9.92 |

EXAMPLE 3

Preparation of 3-butyryl-4-(2-methylphenylamino)-8-(2-dimethylaminoethoxy)quinoline 3-Butyryl-4-(2-methylphenylamino)-8-hydroxyquinoline (3.2 g, 10 mmol) and potassium t-butoxide (5.0 g, 40 mmol) were stirred in dry dimethylformamide at 80° and 2-dimethylaminoethyl chloride hydrochloride (2.9 g, 20 mmol) added. The mixture was stirred for 2 hours, poured into water and extracted with ether. The extracts were dried and evaporated. Chromatography (silica gel, 3-5% methanolic ammonia in dichloromethane) and recrystallisation from ether gave 3-butyryl-4-(2-methylphenylamino)-8-(2-dimethylaminoethoxy)quinoline (1.0 g, 34%), m.p. 88°-90°.

|  | $C_{24}H_{29}N_3O_2.0.1H_2O$ |
|---|---|
| Found | C 73.18, H 7.37, N 10.44 |
| Requires | C 73.29, H 7.46, N 10.68 |

EXAMPLE 4

Preparation of 3-butyryl-4-(2-methylphenylamino)-8-(3-(1-pyrrolidinyl)propoxv)quinoline 3-Butyryl-4-(2-methylphenylamino)-8-hydroxyquinoline (3.2 g, 10 mmol) and potassium t-butoxide (5.0 g, 40 mmol) were dissolved in dry dimethylformamide (100 ml) at 100°, 1-(3-chloropropyl)pyrrolidine hydrochloride (3.6 g, 20 mmol) added, and stirring continued for 1 hour. The mixture was diluted with water and extracted with ether, and the ether extracts dried and evaporated. Chromatography (silica gel, 0-3% methanolic ammonia in chloroform) and recrystallisation from ether gave 3-butyryl-4-(2-methylphenylamino)-8-(3-(1-pyrrolidinyl)propoxy)quinoline (0.35 g, 8.5 %), m.p. 101°-103°.

|  | $C_{27}H_{33}N_3O_2.0.1H_2O$ |
|---|---|
| Found | C 74.66, H 7.60, N 9.59 |
| Requires | C 74.83, H 7.72, N 9.70 |

EXAMPLE 5

Preparation of 3-butyryl-4-(2-methylphenylamino)-8-(3-piperidinopropoxy)quinoline 3-Butyryl-4-(2-methylphenylamino)-8-hydroxyquinoline (3.2 g, 10 mmol) and potassium t-butoxide (5.0 g, 40 mmol) were dissolved in dry dimethylformamide (100 ml) at 80°, then 1-(3-chloropropyl)piperidine hydrochloride (4.0 g, 20 mmol) added and stirred for 1 hour. The mixture was poured into water, extracted with ether, and the extracts dried and evaporated. Chromatography (silica gel, 3-5% methanolic ammonia in dichloromethane) and recrystallisation from ether/petroleum ether gave 3-butyryl-4-(2- methylphenylamino)-8-(3-piperidinopropoxy)quinoline (1.2 g, 27%), m.p. 76°–78°.

|  | C$_{28}$H$_{35}$N$_3$O$_2$ |
| --- | --- |
| Found | C 75.35, H 8.04, N 9.25 |
| Requires | C 75.47, H 7.92, N 9.43 |

EXAMPLE 6

Preparation of
3-butyryl-4-(2-methylphenylamino)-8-(3-morpholinopropoxy)quinoline 3-Butyryl-4-(2-methylphenylamino)-8-hydroxyquinoline (3.2 g, 10 mmol) and potassium t-butoxide (5.0 g, 40 mmol) were stirred in dry dimethylformamide (100 ml) at 100°, then 4-(3-chloropropyl)morpholine hydrochloride (5 0 g, 14 mmol) was added. Heating was continued for 2.5 hours, then the mixture was diluted with water and extracted with ether. The combined extracts were dried and evaporated to an oily residue. Chromatography (silica gel, 3% methanolic ammonia in chloroform) and crystallisation from petroleum ether gave 3-butyryl-4-(2-methylphenylamino)-8-(3-morpholinopropoxy)quinoline (2.6 g, 58 %), m.p. 111°–113°.

|  | C$_{27}$H$_{33}$N$_3$O$_3$ |
| --- | --- |
| Found | C 72.15, H 7.39, N 9.20 |
| Requires | C 72.45, H 7.43, N 9.39 |

EXAMPLE 7

Preparation of
3-butyryl-4-(2-methylphenylamino)-8-(1-hydroxy-2-(1-morpholino)ethyl)quinoline Preparation of
3-butyryl-4-(2-methylphenylamino)-8-oxiranylquinoline 3-Butyryl-4-(2-methylphenylamino)quinoline-8-carbaldehyde (0.5 q, 1.5 mmol) was dissolved in dichloromethane (5 ml) and trimethylsulphonium methylsulphate (0.34 g, 1.8 mmol) and 50% aqueous sodium hydroxide (0.75 ml) added. The mixture was stirred vigorously for 2.5 hours, when a further addition of trimethylsulphonium methylsulphate (0.23 g, 1.2 mmol) and 50% aqueous sodium hydroxide (0.5 ml) was made. After stirring for a further 2 hours the mixture was diluted with water and extracted with dichloromethane. The dried extracts were evaporated to an oil, which was purified by flash chromatography (silica gel, ethyl acetate/chloroform). The product crystallised on trituration with petroleum ether to give 3-butyryl-4-(2-methylphenylamino)-8-oxiranylquinoline (0.28 g, 54%), m.p. 114°–116°.

|  | C$_{22}$H$_{22}$N$_2$O$_2$ |
| --- | --- |
| Found | C 76.33, H 6.41, N 7.75 |
| Requires | C 76.27, H 6.40, N 8.09 |

Preparation of
3-butyryl-4-(2-methylphenylamino)-8-(1-hydroxy-2-(1-morpholino)ethyl)quinoline 3-Butyryl-4-(2-methylphenylamino)-8-oxiranylquinoline (1.0 g, 2.89 mmol) and morpholine (1.0 g, 11.55 mmol) in dioxan (20 ml) were heated under reflux for 9 hours. The dioxan was evaporated and the residue dissolved in ethyl acetate, washed with brine, dried and evaporated to an oil which crystallised from ether. Recrystallisation from dichloromethane/ether gave 3-butyryl-4-(2-methylphenylamino)-8-(1-hydroxy-2-morpholinoethyl)quinoline (0.59 g, 47%), m.p. 135°–137°.

|  | C$_{26}$H$_{31}$N$_3$O$_3$ |
| --- | --- |
| Found | C 71.71, H 7.10, N 9.49 |
| Requires | C 72.03, H 7.21, N 9.69 |

EXAMPLE 8

Preparation of
3-butyryl-4-(2-methylphenylamino)-8-(1-hydroxy-2-dimethylaminoethyl)quinoline A mixture of 3-butyryl-4-(2-methylphenylamino)-8oxiranylquinoline (1.0 g, 2.89 mmol) and 33% w/w dimethylamine in methylated spirits (10 ml) was heated at 95° for 2 hours in a pressure vessel. After cooling and evaporation of the solvent, the residue was purified by flash chromatography (silica gel, methanolic ammonia/dichloromethane) and crystallistion from aqueous ethanol to give 3-butyryl-4-(2-methylphenylamino)-8-(1-hydroxy-2-dimethylaminoethyl)quinoline (0.32 g, 28%), m.p. 95°–96°.

|  | C$_{24}$H$_{29}$N$_3$O$_2$ |
| --- | --- |
| Found | C 73.37, H 7.24, N 10.52 |
| Requires | C 73.63, H 7.47, N 10.73 |

EXAMPLE 9

Preparation of
3-butyryl-4-(2-methylphenylamino)-8-(3-(N-benzyl-N-methylamino)propoxy)quinoline 3-Butyryl-4-(2-methylphenylamino)-8-hydroxyquinoline (3.2 g, 10 mmol) and potassium t-butoxide (5.0 g, 40 mmol) were dissolved in dry DMF (100 ml) and N-(3-chloropropyl)-N-methylbenzylamine hydrochloride (4.1 g, 16 mmol) added. The temperature was raised to 90° and the mixture stirred for 2 hours, then poured into water and extracted with ethyl acetate. Drying, evaporation of the solvent, chromatography (silica gel, 0-3% methanolic ammonia in chloroform) and crystallisation from ether gave 3-butyryl-4-(2-methylphenylamino)-8-(3-(N-benzyl-N-methylamino)-propoxy)quinoline (0.7 g, 15%), m.p. 100°–102°.

|  | C$_{31}$H$_{35}$N$_3$O$_2$ |
| --- | --- |
| Found | C 77.16, H 7.45, N 8.46 |
| Requires | C 77.31, H 7.32, N 8.73 |

EXAMPLE 10

Preparation of 3-butyryl-4-(2-methylphenylamino)-8-(3-(N-methyl-N-(3-phenylpropyl)amino)propoxy)quinoline

Preparation of 3-chloro-N-methyl-N-(3-phenylpropyl)-1-propylamine hydrochloride.

A solution of 3-phenyl-N-methyl-1-propylamine (5.0 g, 3.5 mmol), 1-bromo-3-chloropropane (10 ml, 100 mmol) and triethylamine (10 ml, 72 mmol) in chloroform (50 ml) was allowed to stand at room temperature for 3 days. Evaporation of the solvent and chromatography (silica gel, 2% methanolic ammonia in chloroform) gave the product as an oil (1.7 g, 22%). This was converted to the hydrochloride salt with ethanolic HCl, but failed to crystallise and was used without further purification.

Preparation of 3-butyryl-4-(2-methylphenylamino)-8-(3-(N-methyl-N-(3-phenylpropyl)amino)propoxy)quinoline 3-Butyryl-4-(2-methylphenylamino)-8-hydroxyquinoline (3.2 g, 10 mmol) was dried by azeotroping with toluene, then dissolved in dry ethanol (20 ml). Sodium (0.23 g, 10 mmol) was dissolved in ethanol (15 ml), and added to the hydroxyquinoline. The resulting solution was evaporated, and the solid redissolved in toluene (50 ml). 3-chloro-N-methyl-N-(3-phenylpropyl)-1-propylamine hydrochloride (1.5 g, 5.7 mmol) was added and the mixture heated at reflux under nitrogen for 3 hours. Evaporation of the solvent, chromatography (silica gel, 0–3% methanolic ammonia in chloroform) and crystallisation from ether gave 3-butyryl-4-(2-methylphenylamino)-8-(3-(N-methyl-N-(3-phenylpropyl)amino)propoxy)quinoline (0.9 g, 18%), m.p. 79°–81°.

|  | 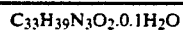$C_{33}H_{39}N_3O_2 \cdot 0.1H_2O$ |
|---|---|
| Found | C 77.38, H 7.71, N 7.92 |
| Requires | C 77.49, H 7.72, N 8.22 |

EXAMPLE 11

Preparation of 3-butyryl-4-(2-methylphenylamino)-8-(3morpholinopropylamino)quinoline

Preparation of ethyl 2-butyryl-3-(2-phthalimidophenylamino)acrylate.

2-Phthalimidoaniline (44.0 g, 0.21 moles) and ethyl 2-butyryl-3-ethoxyacrylate (45 g, 0.21 moles) were heated together in fusion for 10 minutes then allowed to cool, forming a tan solid. The ethyl 2-buryryl-3-(2-phthalimidophenylamino)acrylate (83.0 g, 97%) was stirred in ether, filtered and dried under vacuum, m.p 153°–5° C.

Preparation of 3-butyryl-8-phthalimido-4(1H)quinolone.

Ethyl 2-butyryl-3-(2-phthalimidophenylamino)acrylate (83 g, 0.2 mol) was added portionwise to boiling diphenyl ether and heated under reflux for 45 mins. The mixture was cooled, diluted with hexane and the 3-butyryl-8-phthalimido-4(1H)quinolone (50 g, 67.5%) filtered off, washed with hexane and dried, m.p. 318°–20° C.

Preparation of 3-butyryl-4-chloro-8-phthalimidoquinoline.

3-Butyryl-8-phthalimido-4(1H)quinolone (36 g, 0.1 mol) was heated under reflux in phosphoryl oxychloride (200 ml) for 1 hour. The solvent was evaporated and the residue dissolved in chloroform and poured into a rapidly stirred mixture of ice, water and ammonia then stirred for 10 minutes. The chloroform layer was washed with brine, dried (anhyd. MgSO$_4$), filtered and evaporated to a brown oil. Chromatography (silica gel/5% methanol in chloroform) gave 3-butyryl-4-chloro-8-phthalimidoquinoline as a light brown oil (21.5g, 57%).

Preparation of 3-butyryl-4-(2-methylphenylamino)-8phthalimidoquinoline.

A mixture of 3-butyryl-4-chloro-8-phthalimidoquinoline (61.6 g, 0.16 moles) and o-toluidine (20 ml, 0.19 mol) was heated under reflux in 1,4-dioxan (300 ml) for 3 hours. The solvent was evaporated and the residue was dissolved in chloroform, washed with dil. ammonia solution and brine. The organic solution was dried (anhyd. MgSO$_4$) filtered and evaporated to a dark oil which crystallized on standing to give 3-butyryl-4-(2-methylphenylamino)-8-phthalimidoquinoline (42 g, 58.3%), m.p. b 170°–2° C.

Preparation of 8-amino-3-butyryl-4-(2-methylphenylamino)quinoline.

3-Butyryl-4-(2-methylphenylamino)-8-phthalimidoquinoline (9.0 g, 0.02 moles) and hydrazine hydrate (1.5 ml) were heated together under reflux in ethanol (100 ml) for 2 hours. The solvent was evaporated and the residue was stirred in chloroform, filtered and the filtrate concentrated and chromatographed (silica gel chloroform) to give 8-amino-3-butyryl-4-(2-methylphenylamino)quinoline (5.5 g, 86%), as a bright yellow oil which crystallized on standing, m.p. 108°–10° C.

|  | 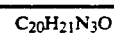$C_{20}H_{21}N_3O$ |
|---|---|
| Found | C 75.01, H 6.58, N 13.06 |
| Requires | C 75.21, H 6.63, N 13.16 |

Preparation of 3-butyryl-4-(2-methylphenylamino)-8-(3 morpholinopropylamino)quinoline.

8-Amino-3-butyryl-4-(2-methylphenylamino)quinoline (6.5 g, 0.02 moles) and 3-chloropropylmorpholine hydrochloride (5.0 g, 0.025 moles) were heated together in fusion (150° C) for 20 minutes. The product was partitioned between ethyl acetate and dil. ammonia solution. The organic layer was washed twice with sodium dihydrogen phosphate solution (pH5), dried, filtered and evaporated. Chromatography (silica gel/chloroform/30–0% hexane) and crystallization from hexane gave 3-butyryl-4-(2-methyl phenylamino)-8-(3-morpholinopropylamino)quinoline as orange crystals (0.45 g, 5%), m.p. 110°–11° C.

|  | 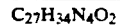$C_{27}H_{34}N_4O_2$ |
|---|---|
| Found | C 72.49, H 7.66, N 12.46 |
| Requires | C 72.61, H 7.67, N 12.55 |

EXAMPLE A

A tablet for oral administration can be prepared by combining

|  | Mg/Tablet |
|---|---|
| Compound of structure (I) | 100 |
| Mannitol | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration can be prepared from the following

| Compound of structure (I) | 6.68% (w:v) |
|---|---|
| 1 M citric acid | 30% (v:v) |
| sodium hydroxide (qs) | to pH 3.2 |
| water for injection EP | to 100 ml |

The compound of structure (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

BIOLOGICAL DATA

$H^{30}K^+$ATPase Activity

The effects of a single high concentration (100 μM) of a compound of structure (I) on K-stimulated ATPase activity in lyophilised gastric vesicles was determined. Preferred compounds of structure (I) were also tested over a range of concentrations to determine IC50 values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) $K^+$-stimulated ATPase activity.

$K^+$-stimulated ATPase activity was determined at 37° C. in the presence of the following : 10 mM Pipes/Tris buffer pH 7.0, 2 mM $MgSO_4$, 1 mM KCl, 2 mM $Na_2ATP$ and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate wa also determined.

The IC50 values obtained for the compounds of examples 1 to 11 in the range of from 0.39 to 3.52 μM.

What is claimed is:

1. A compound of structure (I):

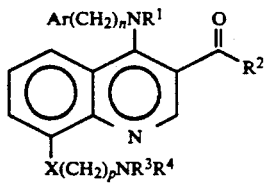

in which
Ar is a phenyl group optionally substituted by 1 to 3 substituents selected from $C_{1-6}$alkyl, $C_{1-6}$alkoxy, amino, $C_{1-6}$-alkylthio, halogen, cyano, hydroxy, carbamoyl, carboxy, $C_{1-6}$alkanoyl or trifluoromethyl; n is 0 to 4;
$R^1$ is hydrogen or $C_{1-6}$alkyl;
$R^2$ is hydrogen, $C_{1-6}$alkyl, $C_{1-6}$alkoxy, $C_{1-6}$alkoxy$C_{1-6}$alkyl, $C_{3-6}$cycloalkyl, $C_{3-6}$cycloalkyl$C_{1-6}$alkyl, phenyl, or phenyl$C_{1-6}$alkyl;
X is CHOH, $NR^1S$, or O;
p is 1 to 6; and
$R^3$ and $R^4$ are the same or different and are each hydrogen, $C_{1-4}$alkyl, or optionally substituted phenyl$C_{1-4}$alkyl or together with the nitrogen atom to which they are attached form a pyrrolidino, piperidino, piperazino or morpholino ring, or a pharmaceutically acceptable salt thereof.

2. A compound according to claim 1 in which n is O, and Ar is a substituted phenyl ring.

3. A compound according to claim 2 in which in Ar the phenyl ring is substituted by a group in the 2-position of the ring.

4. A compound according to claim 3 in which the substituent in the 2-position of the phenyl ring is a methyl group.

5. A compound according to claim 4 in which X is O.

6. A compound according to claim 1 which is 3-butyryl-4-(2-methylphenylamino)-8-(3-dimethylaminopropoxy)quinoline.

7. A compound according to claim 1 which is 3-butyryl-4-(4-fluoro-2-methylphenylamino)-8-(3-dimethylaminopropoxy)quinoline.

8. A compound according to claim 1 which is 3-butyryl-4-(2-methylphenylamino)-8-(2-dimethylaminoethoxy)quinoline.

9. A compound according to claim 1 which is 3-butyryl-4-(2-methylphenylamino)-8-(3-(1-pyrrolidinyl)-propoxy)quinoline.

10. A compound according to claim 1 which is 3-butyryl-4-(2-methylphenylamino)-8-(3-piperidinopropoxy)quinoline.

11. A compound according to claim 1 which is 3-butyryl-4-(2-methylphenylamino)-8-(3-morpholinopropoxy)quinoline.

12. A compound according to claim 1 which is 3-butyryl-4-(2-methylphenylamino)-8-(1-hydroxy-2morpholinoethyl)quinoline.

13. A compound according to claim 1 which is 3-butyryl-4-(2-methylphenylamino)-8-(1-hydroxy-2-dimethylaminoethyl)quinoline.

14. A compound according to claim 1 which is 3-butyryl-4-(2-methylphenylamino)-8-(3-(N-benzyl-Nmethylamino)propoxy)quinoline.

15. A compound according to claim 1 which is 3-butyryl-4-(2-methylphenylamino)-8-(3-(N-benzyl-N-(3-phenylpropyl)amino)propoxy)quinoline.

16. A compound according to claim 1 which is 3-butyryl-4-(2-methylphenylamino)-8-(3-morpholinopropylamino)quinoline.

17. A pharmaceutical composition comprising an effective amount of a compound according to claim 1 or a pharmaceutically acceptable salt thereof and a pharmaceutically acceptable carrier.

18. A method of inhibiting gastric acid secretion which comprises administering to a subject in need thereof an effective amount of a compound according to claim 1.

* * * * *